US00PP36198P2

(12) United States Plant Patent
Ranney et al.

(10) Patent No.: US PP36,198 P2
(45) Date of Patent: Oct. 15, 2024

(54) ***EUONYMUS* PLANT NAMED 'NCEA1'**

(50) Latin Name: *Euonymus alatus*
Varietal Denomination: 'NCEA1'

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan P. Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/590,409

(22) Filed: Feb. 28, 2024

(51) Int. Cl.
*A01H 5/00* (2018.01)
*A01H 6/00* (2018.01)

(52) U.S. Cl.
USPC ..... Plt./246
CPC ..... *A01H 6/00* (2018.05)

(58) Field of Classification Search
USPC ..... Plt./226, 246
See application file for complete search history.

*Primary Examiner* — Karen M Redden

(57) ABSTRACT

A new and distinct cultivar of *Euonymus* plant named 'NCEA1' is disclosed, characterized by plants with compact, rounded habits, good fall color, low fruit production, and greatly reduced fertility. The new cultivar is a *Euonymus*, suitable for ornamental garden purposes.

4 Drawing Sheets

Latin name of the genus and species: *Euonymus alatus*.
Cultivar denomination: 'NCEA1'.

BACKGROUND OF THE INVENTION

The present invention comprises a new and distinct *Euonymus alatus* cultivar hereinafter referred to by the cultivar name 'NCEA1'. This new *Euonymus alatus* was developed through a breeding program at a research nursery located in Mills River, North Carolina. 'NCEA1' was selected from a population of plants derived from gamma irradiated seed of *Euonymus alatus*. 'NCEA1' was found and selected at the same nursery in 2013.

The first asexual propagation of 'NCEA1' occurred in July 2015 by rooting stem cuttings at a research nursery in Mills River, North Carolina. 'NCEA1' roots readily from softwood cuttings treated with a basal dip of 3,000 ppm indole butyric acid (potassium salt) in water. 'NCEA1' was repeatedly reproduced by vegetative cuttings over an eight-year period and has been found to retain its distinctive characteristics through successive asexual propagations.

Date of first sale was Jun. 27, 2023, occurring in Grand Haven, Michigan. This sale was made directly by the inventor or one who obtained the claimed invention directly or indirectly from the inventor. This sale and all public disclosures made between Jun. 27, 2023 and the filing of this application fall within the exception allowed under 102(b)(1).

SUMMARY OF THE INVENTION

The cultivar 'NCEA1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'NCEA1' These characteristics in combination distinguish 'NCEA1' as a new and distinct *Euonymus* cultivar:

1. Low fruit production and greatly reduced fertility.
2. Good fall color.
3. Compact, rounded habit.

COMPARISON TO PARENT VARIETIES

The parent varieties are unknown.

COMMERCIAL COMPARISON

'NCEA1' can be compared to the commercial variety *Euonymus alatus* 'Compactus', unpatented. Plants of the new cultivar 'NCEA1' are similar to plants of " " in most horticultural characteristics, however, plants of the new cultivar 'NCEA1' differ in the following:

1. The new cultivar produces very little seed; this comparator produces abundant seed. Whereas a mature seven-year-old plant of 'NCEA1' produced 23, 24, and 60 fruit in 2019, 2020, and 2021, respectively, a similar sized and aged *Euonymus alatus* 'Compactus', grown next to each other, that produced 3,169, 3,530, and 4,230 seeds for the same years.

BRIEF DESCRIPTION OF THE PHOTOGRAPHS

Flowers, foliage and form of 'NCEA1' are illustrated by the accompanying photographs. The colors shown are as true as can be reasonably obtained by conventional photographic procedures. Colors in the photographs may differ slightly from the color values cited in the detailed botanical description, which accurately describe the colors of the new *Euonymus alatus* 'NCEA1'.

DETAILED BOTANICAL DESCRIPTION

Figure 1:
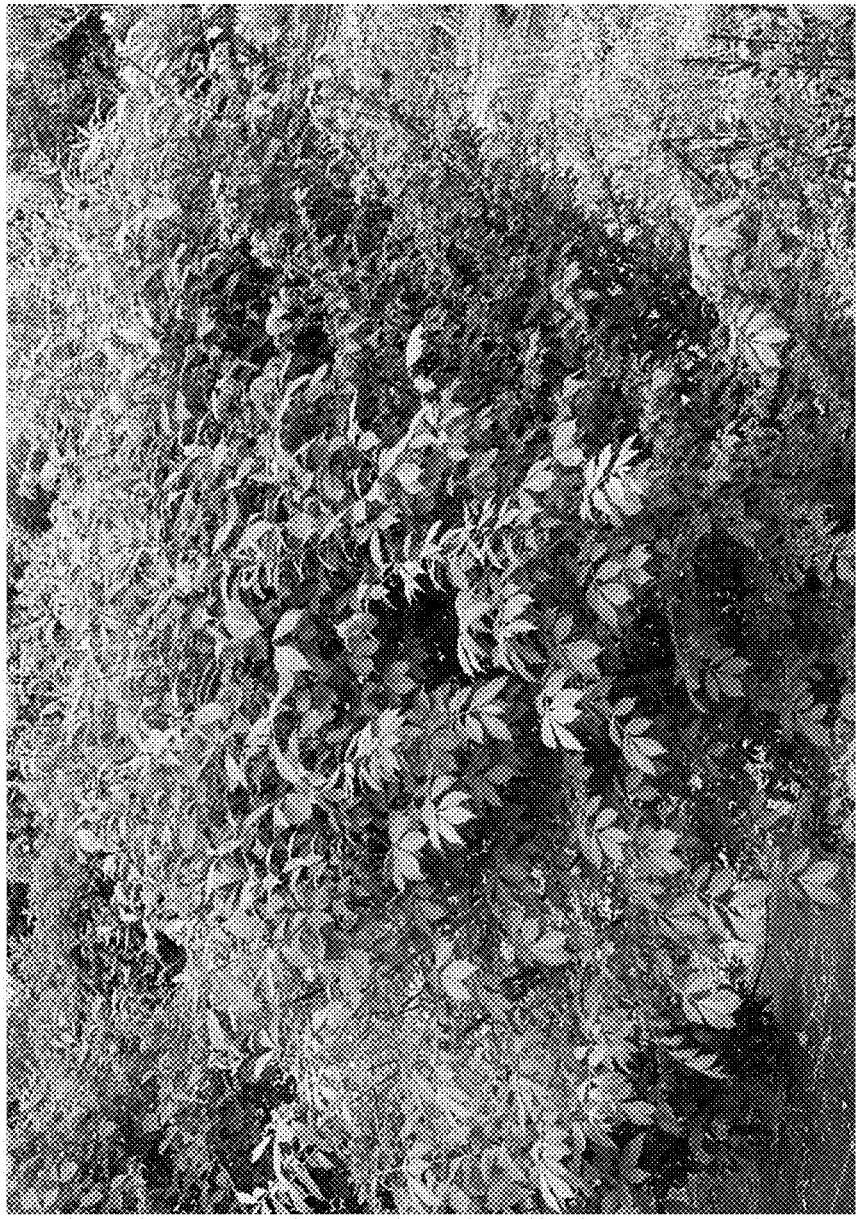
FIG. 1 is a photograph showing the habit of an eight-year-old, field-grown plant during May 2021, in Mills River, North Carolina.
Figure 2:
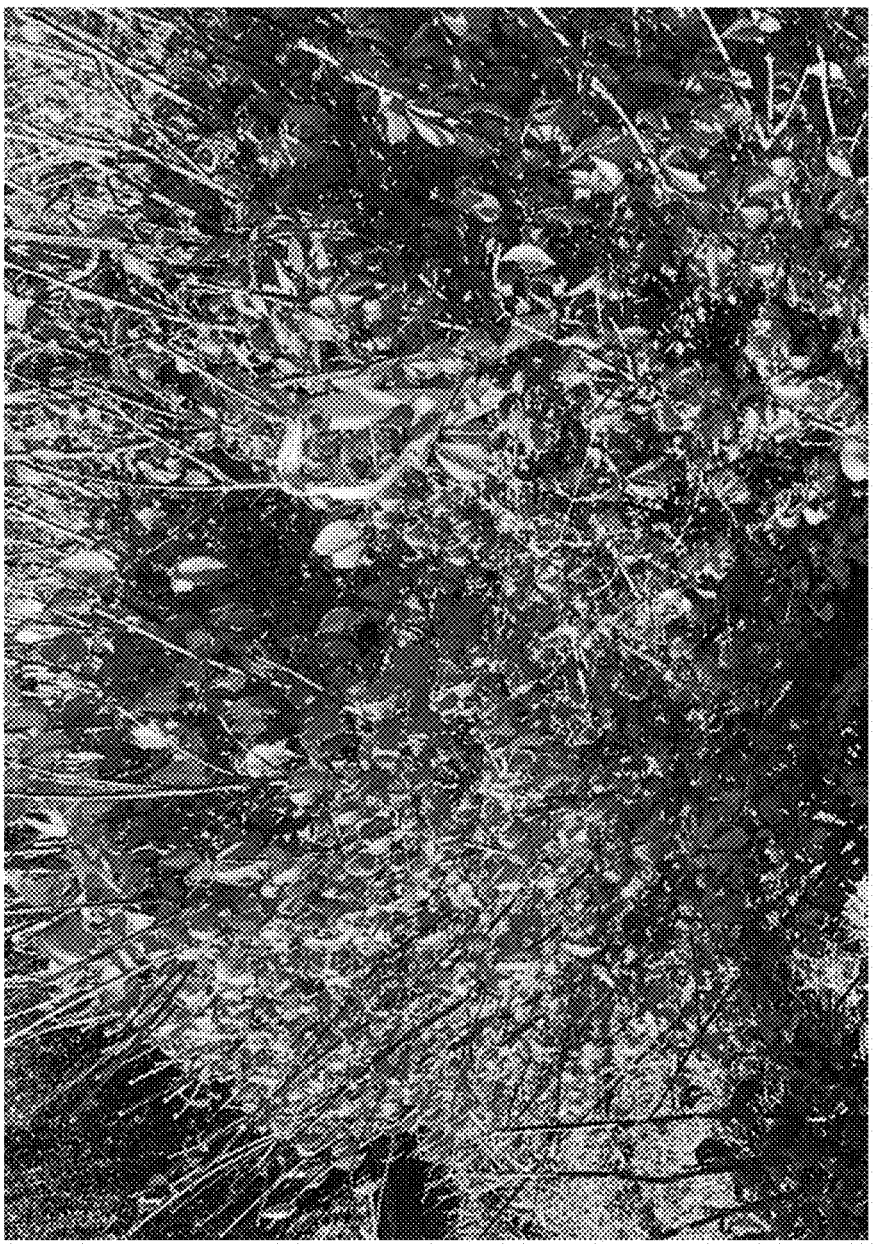
FIG. 2 is a photograph of the fall foliage of an eight-year-old, field-grown plant during November 2021, in Mills River, North Carolina.
Figure 3:
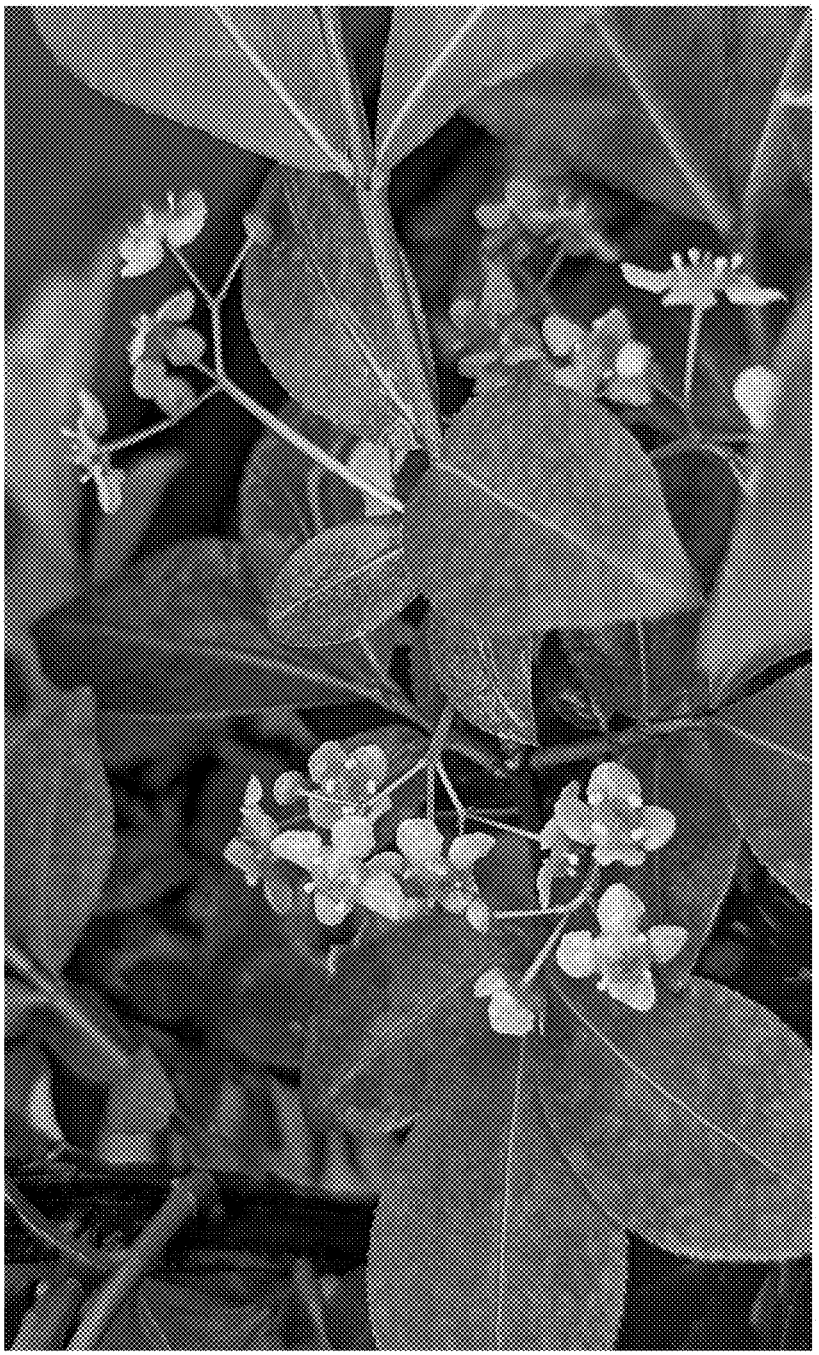
FIG. 3 is a photograph of the spring foliage and flowers of the new cultivar.
Figure 4:
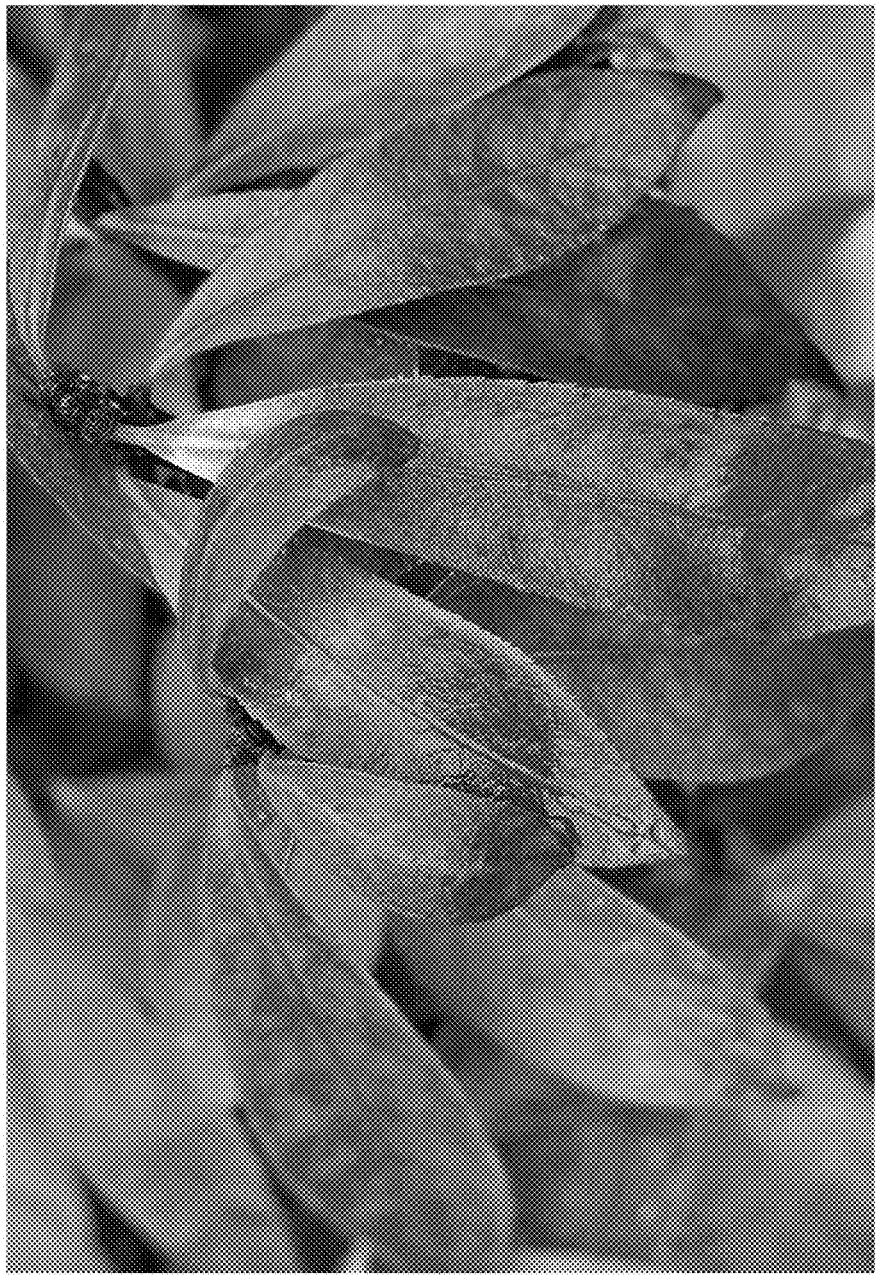
FIG. 4 is a close-up view of foliage changing color from green to red.

The following is a detailed description of the botanical characteristics of the new and distinct *Euonymus alatus* 'NCEA1'. The detailed description was taken on a nine to ten-year-old, field-grown plant in Mills River, North Carolina in fall of 2022 and spring of 2023. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable. Measurements and numerical values represent averages of typical plant types.

Botanical classification: *Euonymus alatus* 'NCEA1'.

PROPAGATION

Method: Softwood cuttings.

Time to rooting: 8 weeks in summer at 68° F.; 10 to 12 weeks in winter at 55° to 60° F.

Root description: Moderately dense, moderate branching, medium thickness, and fibrous. White in color, not accurately measured by The R.H.S. Chart.

PLANT

Plant type: Deciduous shrub.

Growth habit: Compact, rounded.

Height: 150 cm.

Plant spread: 170 cm.

Shoots:

*Current year's growth*.—Length: Average 14.5 cm. Diameter: Average 0.3 cm. Color: RHS Reddish-Brown 175A. Texture: Glabrous with longitudinal corky wings of RHS Gray 201A.

*Prior year's growth*.—Length: Average 17.5 cm. Diameter: Average 0.5 cm. Color: RHS Brown 200C. Texture: Glabrous with longitudinal corky wings of RHS Gray 201A.

Branches:

*Woody branches*.—Length: Average 30 cm. Diameter: Average 2 cm. Color: RHS Brown 200C, mottled with RHS Gray 201A. Texture: Glabrous.

FOLIAGE

Leaf:

*Type*.—Simple.

*Arrangement*.—Opposite.

*Length*.—Average 7.2 cm.

*Width*.—Average 2.7 cm.

*Shape*.—Ovate to obovate.

*Apex*.—Acute.

*Base*.—Cuneate.

*Margin*.—Serrate.

*Texture*.—Top surface: Glabrous. Bottom surface: Glabrous.

*Color*.—Mature foliage upper side: RHS Green 137A. Mature foliage under side: RHS Yellow-Green 146B. Fall foliage upper side: RHS Red-Orange N34A. Fall foliage under side: RHS Red-Orange N34A.

*Venation*.—Type: Pinnate. Venation color upper side: RHS Yellow-Green 146D. Venation color under side: RHS Yellow-Green 146D.

Petiole:

*Length*.—Average 0.4 cm.

*Diameter*.—About 0.1 cm.

*Texture*.—Upper side: Glabrous. Under side: Glabrous.

*Color*.—RHS Yellow-Green 146D.

FLOWER

Inflorescence:

*Flowering season*.—April to May in Mills River, North Carolina.

*Arrangement*.—Perfect flowers arranged in a three to seven-flowered cyme.

*Quantity of flowers per inflorescence*.—3 to 7.

Bud:

*Shape*.—Round.

*Diameter*.—About 0.1 cm.

*Height*.—About 0.1 cm.

*Color*.—RHS Yellow-Green 144A.

*Texture*.—Glabrous.

Flower:

*Shape*.—Cruciform.

*Diameter*.—Average 0.8 cm.

*Height*.—About 0.1 cm.

Petals:

*Number*.—4 per flower.

*Shape*.—Round.

*Length*.—About 0.3 cm.

*Width*.—About 0.3 cm.

*Apex*.—Round.

*Base*.—Round.

*Margin*.—Entire.

*Texture*.—Glabrous.

*Color*.—RHS Yellow-Green 144C.

Sepals:

*Number*.—4.

*Shape*.—Fused into a disk.

*Length*.—About 0.1 cm.

*Width*.—About 0.1 cm.

*Apex*.—Fused.

*Base*.—Fused.

*Margin*.—Entire.

*Texture*.—Glabrous.

*Color*.—RHS Yellow-Green 144A.

Peduncle:

*Length*.—Average 2.4 cm.

*Diameter*.—About 0.1 cm.

*Color*.—RHS Yellow-Green 144A.

*Texture*.—Glabrous.

Pedicels:

*Length*.—About 0.3 cm.

*Diameter*.—Less than 0.1 cm.

*Color*.—RHS Yellow-Green 144A.

*Texture*.—Glabrous.

REPRODUCTIVE ORGANS

Stamens:

*Number*.—4.

*Anthers*.—Shape: Round. Length: Less than 0.1 cm. Color: RHS Yellow 2A. Pollen: Quantity: Average. Color: RHS Yellow 2A.

Pistil:

*Number*.—1.

*Length*.—Less than 0.1 cm.

*Style*.—Length: Less than 0.1 cm. Color: RHS Yellow-Green 144A.

*Stigma*.—Shape: Flattened, irregularly globoid. Color: RHS Yellow-Green 144A.

FRUIT AND SEEDS

Fruit:

*Description*.—Four-lobed capsule that opens to reveal seed with an orange-red seed coat.

*Number of fruit per shrub*.—About 23-60 fruit on six to eight-year-old mature shrub.

Seeds:

*Shape*.—Ovoid.

*Length*.—About 0.6 cm.

*Width*.—About 0.5 cm.

*Seed coat color*.—Vivid Reddish Orange (RHS 34A).

*Seed color*.—RHS Red 180C.

*Texture*.—Glabrous.

OTHER CHARACTERISTICS

Disease and pest resistance: Neither resistance nor susceptibility to normal pests of *Euonymus* observed.

Temperature tolerance: Cold hardy to at least USDA zone 6b; testing has not been completed in colder zones.

What is claimed is:

1. A new and distinct cultivar of *Euonymus* plant named 'NCEA1' as herein illustrated and described.

* * * * *